United States Patent [19]

Yamamoto et al.

[11] Patent Number: 4,529,825

[45] Date of Patent: Jul. 16, 1985

[54] METHOD FOR THE PREPARATION OF A TRANS-ISOMER OF ETHYLENICALLY UNSATURATED ORGANIC COMPOUNDS

[75] Inventors: Akira Yamamoto; Toshinobu Ishihara, both of Niigata, Japan

[73] Assignee: Shin-Etsu Chemical Co., Ltd., Tokyo, Japan

[21] Appl. No.: 583,881

[22] Filed: Feb. 27, 1984

Related U.S. Application Data

[63] Continuation-in-part of Ser. No. 472,181, Mar. 4, 1983, abandoned.

[30] Foreign Application Priority Data

Mar. 15, 1982 [JP] Japan .................................. 57-40524

[51] Int. Cl.$^3$ .......................... C07C 29/17; C07C 5/09
[52] U.S. Cl. ..................................... 568/903; 585/250
[58] Field of Search ................. 568/903, 851; 585/250

[56] References Cited

U.S. PATENT DOCUMENTS 2,777,884  1/1957  Rutledge et al. ................... 568/851
3,225,110 12/1965  Kurtz ................................. 568/851

*Primary Examiner*—J. E. Evans
*Attorney, Agent, or Firm*—Toren, McGeady & Stanger

[57] ABSTRACT

The trans-isomer of an ethylenically unsaturated organic compound of the formula $R^1CH\!=\!CHR^2$, in which $R^1$ and $R^2$ are each a substituted or unsubstituted monovalent hydrocarbon group, is selectively prepared in a high yield by the reduction of the corresponding acetylenically unsaturated organic compound of the formula $R^1C\!\equiv\!CR^2$. The method comprises reducing the starting compound in a hydrocarbon solvent containing an alkali metal dispersed therein in the presence of a proton donor compound such as an alcohol or a carboxylic acid at a temerature of 50° to 150° C.

7 Claims, No Drawings

METHOD FOR THE PREPARATION OF A TRANS-ISOMER OF ETHYLENICALLY UNSATURATED ORGANIC COMPOUNDS

BACKGROUND OF THE INVENTION

This is a continuation-in-part application from a copending U.S. patent application Ser. No. 472,181 filed Mar. 4, 1983, now abandoned.

The present invention relates to a novel method for the preparation of a trans-isomer of ethylenically unsaturated organic compounds. More particularly, the invention relates to a novel method for the preparation of a trans-isomer of an ethylenically unsaturated organic compound by the reduction or partial hydrogenation of a corresponding acetylenically unsaturated compound having the triple bond not at the chain end of the molecule according to which the product contains the trans-isomer in a predominant proportion over the cis-isomer. Such a stereospecific synthesis of an ethylenically unsaturated organic com-pound is sometimes of great significance when the physiological activity of the compound or compounds derived therefrom is the matter of concern since the physiological activities may be quite different between the cis- and trans-isomers of the same organic compound.

There is known a method for the preparation of a trans-isomer of an ethylenically unsaturated organic compound by the selective reduction of a corresponding acetylenically unsaturated organic compound according to the procedure known as the so-called Birch reaction in which the acetylenically unsaturated organic compound is reduced with metallic sodium in liquid ammonia. This method is, however, not advantageous from the standpoint of industrial production of the desired compound since a large volume of liquid ammonia must be used as the reaction medium with great difficulties in handling and, in addition, the reaction vessel must be provided with a special means for chilling the reaction mixture at $-33°$ C. or below at which the reaction is performed.

Therefore, it has been eagerly desired to develop a convenient and industrially advantageous method for the preparation of a trans-isomer of ethylenically unsaturated compounds.

SUMMARY OF THE INVENTION

The object of the present invention is therefore to provide a novel and improved method for the preparation of a trans-isomer of an ethylenically unsaturated organic compound free from the above described disadvantages in the conventional method by the Birch reaction.

The method of the present invention for the preparation of a trans-isomer of an ethylenically unsaturated organic compound, represented by the general formula $R^1CH=CHR^2$, where $R^1$ and $R^2$ are each a substituted or unsubstituted monovalent hydrocarbon group, by the selective reduction of the corresponding acetylenically unsaturated organic compound represented by the general formula $R^1C\equiv CR^2$, where $R^1$ and $R^2$ each have the same meaning as defined above, comprises reducing the acetylenically unsaturated organic compound in a hydrocarbon solvent containing an alkali metal dispersed therein in the presence of a proton donor compound. The reaction of reduction is performed usually at a temperature in the range from 50° to 150° C.

The advantages of the inventive method are obtained by the use of a hydrocarbon solvent easy to handle as the reaction medium in place of the liquid ammonia in the prior art method by the Birch reaction and also by the reaction temperature of 50° to 150° C., instead of $-33°$ C. or below, readily obtained without using an expensive freezing or chilling unit.

DETAILED DESCRIPTION OF THE PREFERRED EMBODIMENTS

As a natural consequence of the object of the invention, the acetylenic triple bond in the starting acetylenically unsaturated compound should not be at the chain end but the starting compound is represented by the general formula $R^1C\equiv CR^2$, in which $R^1$ and $R^2$ are each a substituted or unsubstituted monovalent hydrocarbon group without particular limitation but cannot be a hydrogen atom.

In particular, several alkenyl or alkadienyl acetate compounds are known to have an activity as a sex pheromone of some insects only when the compound has a trans configuration. Such an alkenyl or alkadienyl acetate of trans configuration can be readily prepared utilizing the inventive method in which the group $R^1$ is an alkyl or alkenyl group and $R^2$ is a hydroxy-substituted alkyl group in the starting acetylenic compound to give an alkenyl or alkadienyl alcohol having the trans configuration which is then acetylated into the acetate. Exemplary of such alkenyl or alkadienyl alcohol are trans-3-hexen-1-ol from 3-hexyn-1-ol, trans-3-octen-1-ol from 3-octyn-1-ol, E,Z-3,13-octadecadienol from Z-13-octadecaen-yn-3-ol-1 and the like. trans-2-Octene and the like olefin compounds having the trans configuration can also be prepared by the inventive method from, for example, octyne-2.

As is mentioned above, the reaction according to the inventive method is carried out in a medium of a hydrocarbon solvent in which an alkali metal is finely dispersed. Such a dispersion of an alkali metal, preferably metallic sodium, in a hydrocarbon solvent can be readily prepared by vigorously agitating the hydrocarbon solvent together with a calculated amount of the alkali metal at a temperature higher than the melting point of the alkali metal. The temperature should be, for example, 100° C. or higher when the alkali metal is metallic sodium.

The hydrocarbon solvents suitable for use in the inventive method are not particularly limitative but should preferably have a boiling point higher than the melting point of the alkali metal as exemplified by toluene, xylene, cumene, ethylbenzene, decahydronaphthalene and the like and suitable alkali metals include metallic sodium and potassium, of which metallic sodium is preferred.

In carrying out the selective reduction of an acetylenically unsaturated organic compound in a medium of a hydrocarbon solvent containing an alkali metal dispersed therein in the presence of a proton donor compound into the desired trans-isomer of the corresponding ethylenically unsaturated organic compound, the alkali metal should preferably be contained in the reaction medium as dispersed therein in an amount of 2 to 5 moles per mole of the starting acetylenically unsaturated organic compound. Although the theoretically required amount of the alkali metal is 2 moles per mole of the starting unsaturated compound, the yield of the desired product is somewhat improved by use of an excess amount of the alkali metal over 2 moles while no further improvement can be obtained even by the use thereof in excess of 5 moles per mole of the starting unsaturated compound.

The method of the present invention is very versatile in respect of the types of the acetylenically unsaturated organic compounds as the starting reactant and a variety of such acetylenic compounds can be selectively reduced including, for example, 3-hexyn-1-ol, 3-octyn-1-ol, Z-13-octadecaen-yn-3-ol-1, octyne-2 and the like although, needless to say, acetylene, butyne-1 and the like acetylenic compounds having the triple bond at the chain end of the molecule are excluded from the starting reactant in the inventive method.

The proton donor compound, which should be present in the reaction mixture to motivate the reducing reaction, is exemplified by alcoholic compounds such as methyl alcohol, ethyl alcohol, ethylene glycol and the like and carboxylic acids such as acetic acid and the like as well as, though less preferable, water which may be used in combination with the alcoholic proton donor compound. It should be noted that, when the starting acetylenically unsaturated compound as the reactant is itself an alcoholic compound or a carboxylic acid, the reactant per se can be the proton donor compound. The amount of the proton donor compound to be added to the reaction mixture should be at least equivalent to the alkali metal dispersed in the medium of the hydrocarbon solvent in order to fully exhibit the reducing power as the proton source and to leave no unreacted free alkali metal.

It is furthr noted that, although some acetylenic compounds such as acetylene and butyne-1 having the triple bond at the chain end of the molecule may serve as a proton donor compound, such a compound is not suitable as a proton donor compound used in the inventive method since the compound readily reacts with the alkali metal to form an acetilide compound of the alkali metal resulting in the increased loss of the alkali metal.

Although there is no particular limitation in carrying out the method of the present invention in respect of the order of introducing the reactants and other materials pertaining to the reaction into the reaction vessel to form the reaction mixture, the reaction is conveniently performed by first dispersing the alkali metal into the hydrocarbon solvent to form a dispersion into which the starting acetylenically unsaturated organic compound is added followed by the introduction of the proton donor compound to effect the reaction or by simultaneously introducing the starting acetylenically unsaturated organic compound into the hydrocarbon solvent in the course of the preparation of the dispersion of the alkali metal therein followed by the addition of the proton donor compound to the thus formed dispersion to effect the reaction.

When the acetylenically unsaturated organic compound as the starting reactants is itself an alcohol or carboxylic acid capable of acting as a proton donor compound assuming that the number of the -OH group per molecule thereof is only one, a half of the protons theoretically required for the reaction is supplied by the reactant per se although the practical proportion of sufficiency is only 30 to 40% due to the loss of hydrogen in the reaction necessitating supplementary addition of an auxiliary proton donor compound which should be added to the reaction mixture after completion of the reaction without the auxiliary proton donor compound.

The reaction temperature is desirably in the range from 50° to 150° C. or, preferably, at a temperature higher than the melting point of the alkali metal since the reaction velocity is impractically low at a temperature below 50° C. while the yield of the desired trans-isomer of the ethylenically unsaturated organic compound is decreased when the reaction is performed at a temperature higher than 150° C. due to the more predominant side reactions.

According to the above described method of the present invention, numbers of the trans-isomers of ethylenically unsaturated organic compounds can be advantageously prepared to be useful as such or as intermediates for the synthesis of valuable organic compounds including perfumes such as trans-3-hexen-1-ol and the like and sex pheromones of noxious insects or intermediates thereof such as E-11-tetradecenal, E,Z-3,13-octadecadienyl acetate and the like as well as intermediates for the synthesis of agricultural chemicals and medicines.

Following are the examples to illustrate the inventive method in further detail.

EXAMPLE 1

Into a flask of 1 liter capacity equipped with a reflux condenser, a dropping funnel, a thermometer and a stirrer were introduced 23 g (1 mole) of metallic sodium and 400 ml of toluene and the metallic sodium was dispersed in the toluene at 100° C. with vigorous agitation under an atmosphere of nitrogen gas. Then, 45 g (0.46 mole) of 3-hexyn-1-ol were added dropwise into the above prepared dispersion of metallic sodium in toluene kept at a temperature of 98° to 101° C. under agitation and further 19 g (0.29 mole) of ethylene glycol were added thereto dropwise while the reaction mixture was kept at the same temperature as above to effect the reducing reaction.

After cooling, the reaction mixture was neutralized by adding 170 ml of a 20% hydrochloric acid while still in the atmosphere of nitrogen gas followed by phase separation into organic and aqueous solutions. Rectifying distillation of this organic solution gave 40 g of a fraction which was identified to be trans-3-hexen-1-ol. The yield was about 87% of the calculated value.

EXAMPLE 2

Substantially the same experimental procedure as in Example 1 was repeated excepting the replacement of the toluene with the same volume of 1,2-xylene, 45 g of the 3-hexyn-1-ol with 58 g (0.46 mole) of 3-octyn-1-ol and 19 g of the ethylene glycol with 18 g (0.51 mole) of methyl alcohol. Phase separation of the reaction mixture after completion of the reducing reaction followed by the rectifying distillation of the organic solution gave 50 g of a fraction which was identified to be trans-3-octen-1-ol. The yield was about 85% of the calculated value.

EXAMPLE 3

Substantially the same experimental procedure as in Example 1 was repeated excepting the replacement of 45 g of the 3-hexyn-1-ol with 106 g (0.4 mole) of Z-13-octadecaen-yn-3-ol-1. Phase separation of the reaction mixture after completion of the reducing reaction followed by rectifying distillation of the organic solution gave 95 g of a fraction which was identified to be E,Z-3,13-octadecadienol. The yield was about 89% of the calculated value.

This product compound could be converted by acetylation in a conventional procedure to E,Z-3,13- octadecadienyl acetate which is known as the sex pheromone compound of notorious noxious insect "kosukashiba".

EXAMPLE 4

Into a flask as used in Example 1 were introduced 23 g of metallic sodium, 300 ml of decahydronaphthalene and 44 g (0.4 mole) of octyne-2 and the metallic sodium was dispersed in the reaction mixture at 120° C. with vigorous agitation under an atmosphere of nitrogen gas. Then, 62 g (1.03 moles) of acetic acid were added dropwise into the reaction mixture kept at a temperature of 110° to 120° C. to effect the reducing reaction. After cooling, the reaction mixture was admixed with 200 ml of water and subjected to phase separation into organic and aqueous solutions. Rectifying distillation of the organic solution gave 35 g of a fraction which was identified to be trans-2-octene. The yield was about 79% of the calculated value.

EXAMPLE 5

The same experimental procedure as in Example 1 was repeated excepting the replacement of the ethylene glycol as the proton donor compound with a mixture of 13.8 g (0.3 mole) of ethyl alcohol and 5.4 g (0.3 mole) of water. trans-3-Hexenol-1 was obtained in a yield of 31 g corresponding to about 67% of the calculated value.

What is claimed is:

1. A method for the preparation of a trans-isomer of an ethylenically unsaturated organic compound represented by the general formula $R^1CH=CHR^2$, in which $R^1$ and $R^2$ are each a substituted or unsubstituted monovalent hydrocarbon group, by the selective reduction of the corresponding actylenically unsaturated organic compound represented by the general formula $R^1C\equiv CR^2$, in which $R^1$ and $R^2$ each have the same meaning as defined above, which comprises reducing the acetylenically unsaturated organic compound by heating in a hydrocarbon solvent containing an alkali metal dispersed therein in the presence of a proton donor compound selected from the group consisting of methyl alcohol, ethyl alcohol and ethylene glycol, and acetic acid, at a temperature in the range from 50° to 150° C.

2. The method as claimed in claim 1 wherein the alkali metal is metallic sodium.

3. The method as claimed in claim 1 wherein the hydrocarbon solvent is selected from the group consisting of toluene, xylene, cumene, ethylbenzene and decahydronaphthalene.

4. The method as claimed in claim 1 wherein the amount of the alkali metal is in the range from 2 to 5 moles per mole of the acetylenically unsaturated organic compound.

5. The method as claimed in claim 1 wherein the amount of the proton donor compound is at least equivalent to the alkali metal.

6. The method as claimed in claim 1 wherein the reduction of the acetylenically unsaturated organic compound is carried out by the successive steps of:
   (a) dispersing the alkali metal in the hydrocarbon solvent to form a dispersion thereof;
   (b) adding the acetylenically unsaturated organic compound to the said dispersion of the alkali metal in the hydrocarbon solvent to form a reaction mixture; and
   (c) adding the proton donor compound to the said reaction mixture.

7. The method as claimed in claim 1 wherein the reduction of the acetylenically unsaturated organic compound is carried out by the successive steps of:
   (a) dispersing and dissolving the alkali metal and the acetylenically unsaturated organic compound simultaneously in the hydrocarbon solvent to form a reaction mixture; and
   (b) adding the proton donor compound to the said reaction mixture.

* * * * *